(12) United States Patent
Clerc et al.

(10) Patent No.: US 6,991,646 B2
(45) Date of Patent: Jan. 31, 2006

(54) METHOD AND APPARATUS FOR DELIVERING A STENT INTO A BODY LUMEN

(75) Inventors: Claude O. Clerc, Flemington, NJ (US); Kimberly Ann Fischer, Hatfield, PA (US)

(73) Assignee: Linvatec Biomaterials, Inc., Largo, FL (US)

( * ) Notice: Subject to any disclaimer, the term of this patent is extended or adjusted under 35 U.S.C. 154(b) by 407 days.

(21) Appl. No.: 10/024,920

(22) Filed: Dec. 18, 2001

(65) Prior Publication Data
US 2003/0114909 A1    Jun. 19, 2003

(51) Int. Cl.
*A61F 2/06* (2006.01)

(52) U.S. Cl. .................................... 623/1.11
(58) Field of Classification Search ............. 623/1.11, 623/1.18, 1.19, 1.2, 1.23; 606/191–194
See application file for complete search history.

(56) References Cited

U.S. PATENT DOCUMENTS

| | | | |
|---|---|---|---|
| 4,655,771 A | 4/1987 | Wallsten | 623/1 |
| 5,026,377 A | 6/1991 | Burton et al. | 606/108 |
| 5,453,090 A | 9/1995 | Martinez et al. | 604/53 |
| 5,514,154 A * | 5/1996 | Lau et al. | 623/1.15 |
| 5,843,117 A * | 12/1998 | Alt et al. | 623/1.15 |
| 5,935,135 A | 8/1999 | Bramfitt et al. | 606/108 |
| 6,048,350 A | 4/2000 | Vrba | 606/108 |
| 6,123,712 A * | 9/2000 | Di Caprio et al. | 606/108 |
| 6,168,621 B1 * | 1/2001 | Vrba | 623/1.2 |
| 6,629,994 B2 * | 10/2003 | Gomez et al. | 623/1.15 |

* cited by examiner

*Primary Examiner*—(Jackie) Tan-Uyen T. Ho
(74) *Attorney, Agent, or Firm*—Synnestvedt & Lechner LLP

(57) ABSTRACT

Method and apparatus for delivering a stent, including, but not limited to, a self expanding stent, into a body lumen. The apparatus comprises an outer tube having a proximal end and a distal end and sized to hold a stent therein in a radially constricted condition, an inner tube within the outer tube and having a proximal end and a distal end, and a holding element comprising one or more inflatable balloons carried on the inner tube at the location of the loaded stent. The balloon can be inflated prior to the procedure so that the balloon presses against the inner surface of the outer tube trapping the stent in its longitudinal position between the inner and outer tubes. Accordingly, the outer tube can be slid proximally to release the stent or distally to retract the stent back into the delivery device without the stent inadvertently sliding.

20 Claims, 8 Drawing Sheets

METHOD AND APPARATUS FOR DELIVERING A STENT INTO A BODY LUMEN

FIELD OF THE INVENTION

The invention pertains to the delivery of stents and the like into body lumens. More particularly, the invention pertains to the releasing of self-expanding stents and the like from the delivery apparatus.

BACKGROUND OF THE INVENTION

Stents, such as braided or knitted stents for surgical implantation in body lumens (tubular vessels), are known for repairing or strengthening the vessels. A stent essentially is a hollow tube that supplements the body lumen. With respect to the medical condition of stenosis, in which a body lumen tends to collapse or otherwise close, the stent supports the wall of the vessel to prevent it from collapsing or closing. A blood vessel that is narrowed due to the build up of intra-vascular plaque is one example of a stenosis. With respect to the medical condition of aneurism, in which a body lumen is weakened and cannot properly withstand the internal pressure within the vessel and bulges out or ruptures, a stent graft serves essentially the opposite function in that it substitutes for or supplements a weakened portion of the vessel. Stents are known for insertion in blood vessels, bile ducts, colons, trachea, esophagi, urethra, ureters, nasal passages, ductal systems, etc.

Stents are known that are fabricated from rigid, but flexible materials that, when bent by force, tend to retain the bent shape. Such stents may be inserted into the body lumen in an unstressed radially minimal shape while mounted over a deflated balloon. When the stent is in situ, the balloon is inflated in order to radially expand the stent, which will then retain the radially expanded shape after the balloon is deflated and removed.

Another type of stent is termed a self-expanding stent. Self-expanding stents can be compressed radially, but will expand to their original shape once the radially constrictive force is removed. Some types of self-expanding stent are formed from materials that are superelastic or have shape memory characteristics. Such stents are commonly made of Nitinol, a biocompatible alloy that, depending on its chemical composition and thermomechanical history, may be either a shape memory material or a superelastic material. The ULTRAFLEX stent manufactured and sold by Boston Scientific Corporation is an example of a knitted Nitinol stent.

Another type of self-expanding stent that reverts to its original shape due to an elastic deformation when radially compressed is exemplified in U.S. Pat. No. 4,655,771, issued to Wallsten and incorporated herein by reference. Wallsten discloses a self-expanding, braided surgical dilator stent particularly adapted for coronary dilation, but which can be adapted for use in other body vessels. That patent discloses a stent generally in accordance with the stent 10 shown in FIG. 1A. It comprises a hollow tubular member, the wall of which is formed of a series of individual, flexible, thread elements 12 and 14, each of which extends helically around the central longitudinal axis of the stent. A first subset of the flexible thread elements 12 have the same direction of winding and are displaced relative to each other about the cylindrical surface of the stent. They cross a second plurality of helical thread elements 14 which are also displaced relative to each other about the cylindrical surface of the stent, but having the opposite direction of winding. Accordingly, as shown in FIG. 1A, the threads 12 of the first subset cross the threads 14 of the second subset at crossing points 16.

As the stent is axially stretched, i.e., as the longitudinal ends 18 and 20 are forced away from each other, the diameter reduces, as shown in FIG. 1B. Likewise, if the wall of the stent is radially constricted so as to reduce the stent's diameter, the stent elongates. In other words, radial constriction and axial elongation go hand in hand. When the force is released, the stent tends to spring back to its resting diameter and length.

Bioabsorbable stents also are known in the prior art, including bioabsorbable braided self expanding stents of the type generally disclosed in the aforementioned Wallsten patent. Bioabsorbable stents are manufactured from materials that dissolve over an extended period of time when exposed to bodily fluids and are absorbed into the surrounding cells of the body.

Various bioabsorbable materials that are suitable for fabricating stents are known in the prior art, including polymers such as poly-L,D-lactic acid, poly-L-lactic acid, poly-D-lactic acid, polyglycolic acid, polylactic acid, polycaprolactone, polydioxanone, poly(lactic acid-ethylene oxide) copolymers, or combinations thereof. Vainionp et al., Prog Polym. Sci., vol. 14, pp. 697–716 (1989); U.S. Pat. Nos. 4,700,704, 4,653,497, 4,649,921, 4,599,945, 4,532,928, 4,605,730, 4,441,496, and 4,435,590, all of which are incorporated herein by reference, disclose various compounds from which bioabsorbable stents can be fabricated.

Most, if not all, stents need to be radially constricted, i.e., reduced in diameter from their deployment radius, so that they can be inserted into the body lumen. Then, once they are in situ, the stent can be released and radially expanded.

Various insertion apparatus for delivering a stent into a body lumen in a radially constricted state and then releasing stent so that it self expands within the body lumen are available. In one popular design illustrated in FIG. 2 and exemplified, for instance, in U.S. Pat. No. 5,026,377, the delivery apparatus comprises an inner core tube 5 surrounded by a concentric outer tube 1. The outer tube is shorter than the inner tube so that the inner tube can extend from the outer tube at both ends of the delivery device. A handle 6 typically is provided at the proximal end of the inner tube 5. Another handle 2 is provided at the proximal end of the outer tube. The inner tube 5 is slidable within the outer tube by relative manipulation of the two handles. A stent 11 is loaded on the delivery apparatus trapped between the core and the outer tube near the distal end of the delivery apparatus.

The inner tube 5 may be hollow and adapted to accept a guide wire 8 which, as is well known in the related arts, can be used to help guide the distal end of the delivery device to the stent deployment site in the body lumen 4.

During stent delivery, a physician typically will make an incision in the body lumen at a location remote from the stent deployment site and then guide the stent delivery device into the body lumen until the distal end of the stent delivery device is at the stent deployment site. The outer tube is then pulled back out while the inner tube is held in position. Accordingly, the outer tube slides over the stent, thus releasing it from radial constriction, whereby the stent radially expands and contacts the wall of the body lumen and is held in place by frictional force between the lumen wall and the stent body resulting from the radial expansion force of the stent. The stent is now fully deployed and the delivery device can be retracted.

Sometimes, after the stent has been partially released from the delivery device, the physician may decide that the stent is not properly positioned. In such a case, the physician will push the outer tube distally (or draw the inner tube proximally) to retract the stent back into the outer tube and then move the delivery device to a better position to redeploy the stent. Generally, once a self expanding stent is fully released from the delivery device, it cannot be recaptured within the delivery device because the proximal end of the stent has been released from radial constriction and is now bigger than the outer tube and, there is no way to radially constrict it again.

It can be seen from the description above that, during release of the stent in the body lumen, the outer tube must move proximally while the stent and inner tube remain stationary. Likewise, in the case of the need to retract the stent back into the outer tube, the stent must remain stationary as the outer tube is pushed distally back over the stent. However, since the stent, and especially self expanding stents, may exert a radially outward force in the inner wall of the outer tube, the stent may get pulled along with the outer tube due the frictional engagement of the stent and the outer tube.

Aforementioned U.S. Pat. No. 5,026,377 discloses a technique adapted to ensure that the stent remains stationary and fixed to the inner tube when the outer tube is moved relative thereto. That patent discloses a gripping member on the inner tube adjacent the stent, the gripping member comprising a high friction, enlarged diameter portion of the inner tube. The material of the gripping member may take a set around the stent, i.e., locally deform around the threads of the stent as the stent is compressed against the gripping member by the outer tube thereby gripping the stent. The surface of the gripping member may or may not be roughened to increase its ability to grip the stent.

SUMMARY OF THE INVENTION

The invention is a method and apparatus for delivering a stent, including, but not limited to, a self expanding stent, into a body lumen. The apparatus comprises an outer tube having a proximal end and a distal end and sized to hold a stent therein in a radially constricted condition, an inner tube within the outer tube and having a proximal end and a distal end, and one or more inflatable balloons carried on the inner tube at the location of the loaded stent. The balloon can be inflated prior to the procedure so that the balloon presses against the inner surface of the outer tube trapping the stent in its longitudinal position between the inner and outer tubes. Accordingly, the outer tube can be slid proximally to release the stent or distally to retract the stent back into the delivery device without the stent inadvertently sliding.

The balloon(s) should be inflated to an internal pressure or volume that is low enough that the frictional force between the balloon(s) and the inner surface of the outer tube is not so great that it is impossible or difficult to slide the outer tube relative to the inner tube and balloon(s), yet high enough to keep the stent from moving with respect to the inner tube when the outer tube is slid relative to the inner tube and the balloon(s). The balloon(s) may, but need not, be longitudinally aligned with the stent. In embodiments in which the balloon actually forces the loaded stent against the outer tube, the balloon is preferably formed of a material that is more compliant than the outer tube so that the balloon will take a greater set against the stent than the outer tube and hold it in place longitudinally when the outer tube is moved longitudinally relative to the balloon.

The balloon may remain inflated until the stent is fully released from the delivery device, at which point the balloon can be deflated and the delivery device fully removed from the lumen and the procedure concluded.

DETAILED DESCRIPTION OF THE INVENTION

Figure 1A:
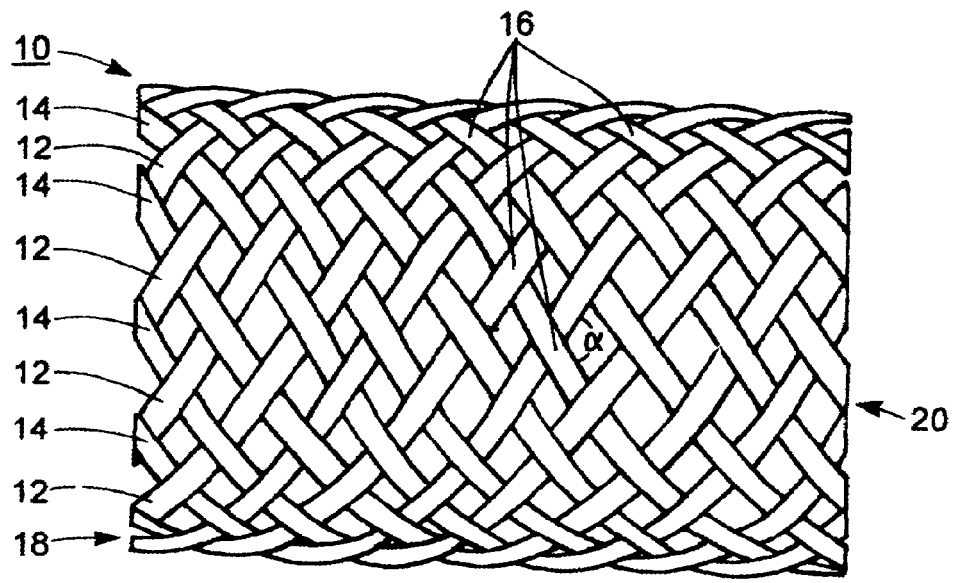
FIG. 1A is a plan view of a braided self expanding stent in accordance with the prior art.
Figure 1B:
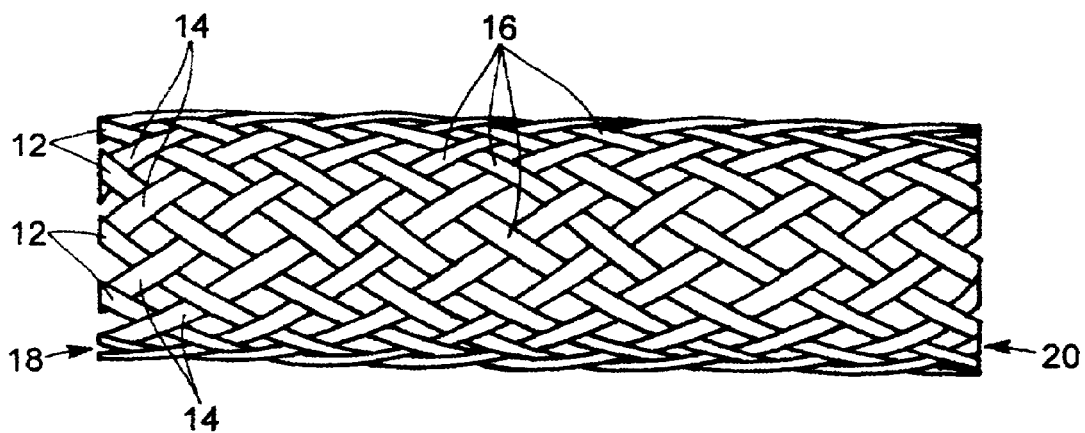
FIG. 1B is a plan view of the stent of FIG. 1A shown in a radially constricted/axially elongated state.
Figure 2:
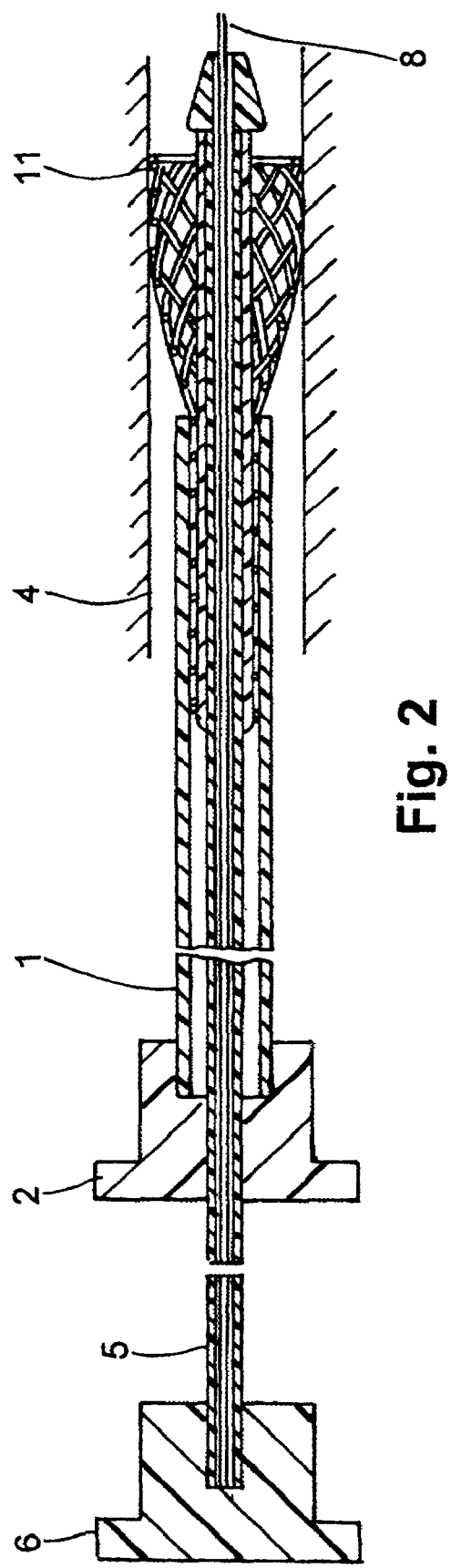
FIG. 2 is a cross sectional view of a conventional stent and stent delivery apparatus.
Figure 3:
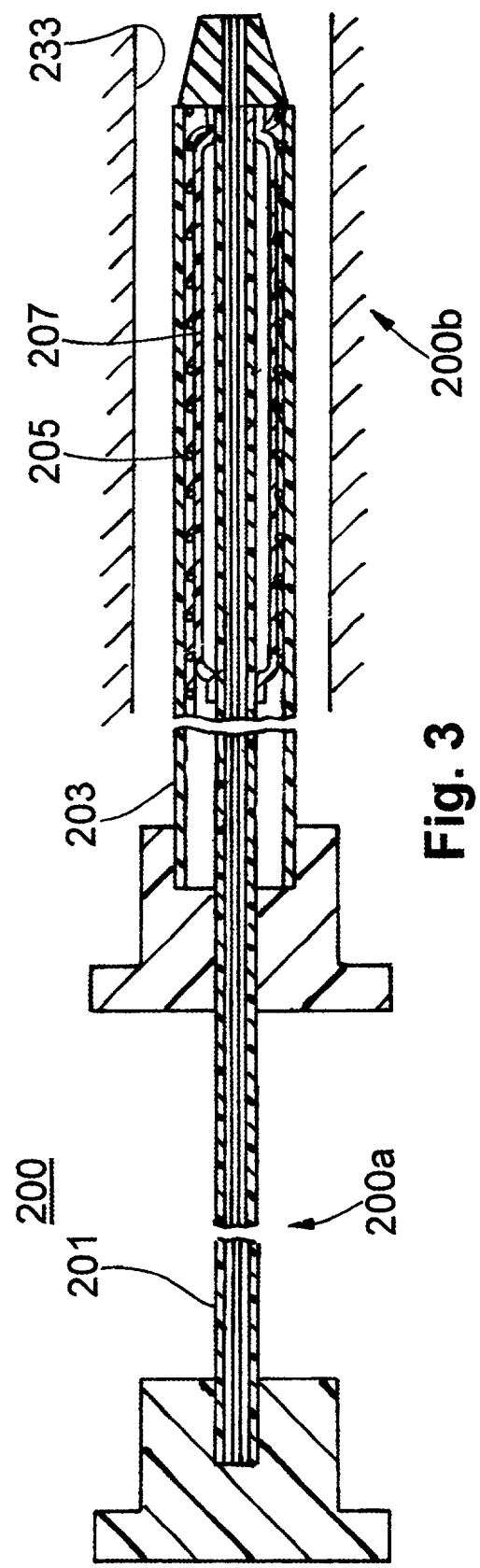
FIG. 3 is a cross sectional view of a stent and stent delivery apparatus in accordance with the present invention.

FIG. 3 is a cross sectional view of the primary elements of a stent and stent delivery device in accordance with one particular embodiment of the present invention. It will be understood by those of skill in the art that certain components that are not particularly relevant to the present invention, such as handles and an optional guide wire, are not shown for sake of clarity. The delivery device 200 has a proximal end 200a and a distal end 200b. The proximal end is the end that is in the physician's hand during a medical procedure. The distal end is the end that is inserted into the lumen during a medical procedure. The device 200 includes an inner tube 201 and an outer tube 203 and a stent 205 captured in a radially constricted condition between the outer tube 203 and the inner tube 201. For exemplary purposes, let us assume that the stent 205 is a bioabsorbable braided self expanding stent.

A balloon 207 is located on the inner tube 201 at the distal end of the delivery device 200 and longitudinally aligned with the loaded stent 205. While, in this particular example, the length of the balloon is shorter than the length of the stent, this is not necessary. The balloon may be longer than the stent or shorter than the stent. In fact, the balloon may comprise multiple, smaller balloons.

The balloon may be inflated to a predetermined pressure or volume during manufacture of the delivery device and sealed with no further mechanism for inflating or deflating the balloon.

Alternately, the balloon may be inflatable and deflatable by the physician. In one such embodiment, an inflation tube runs from the proximal end of the delivery device 200 to the balloon. The inflation tube may or may not be adhered to the inner tube or integrally formed with the inner tube. In other embodiments, the inner tube 201 itself can serve as the inflation tube, without the need for a separate, third tube for inflation. Such embodiments are particularly suitable in connection with stent delivery devices that are not used in connection with a guide wire and thus the inner tube may be closed at its distal end. At the proximal end of the delivery device, the inflation tube can be connected to a pump or syringe for pumping fluid into the balloon to inflate it. The inflation fluid may be a gas, such as nitrogen or air, or a liquid, such as saline, silicone solution, oil or contrast medium. Alternately, the inflation medium could be a foam. The inflation medium should be biocompatible in case it escapes from the balloon while in the body lumen.

The proximal end of the balloon 207 is sealed over the inner tube so as to be air tight, except through the bore in the inflation tube in embodiments in which the balloon is inflatable by the physician. The distal end of the balloon is also sealingly attached to the inner tube, such as by adhesive or a wire tightly wound around each end of the balloon. In one embodiment, the distal end of the balloon is rolled over and bonded to the inner tube. Alternatively, the distal end of the balloon may instead simply bonded to the inner tube without rolling over.

The balloon 207 can be inflated anytime before the outer tube is moved relative to the stent and inner tube. This may be done prior to inserting the delivery apparatus into the lumen or after the delivery apparatus is inserted into the lumen and the stent is in the desired location for deployment, but before the outer tube 203 is withdrawn. The inflation medium may be applied at the proximal end of the inflation tube by syringe or by coupling the inflation tube to another tube coupled to a pump. The balloon 207 is inflated so that it presses the stent 205 against the inner surface of the outer tube 203. The pressure or volume to which the balloon is inflated should be selected so as to exert sufficient frictional force against the stent as it is pressed against the inner wall of the outer tube, yet low enough that it is not impossible or difficult to slide the outer tube relative to the stationary stent and balloon.

Figure 4:
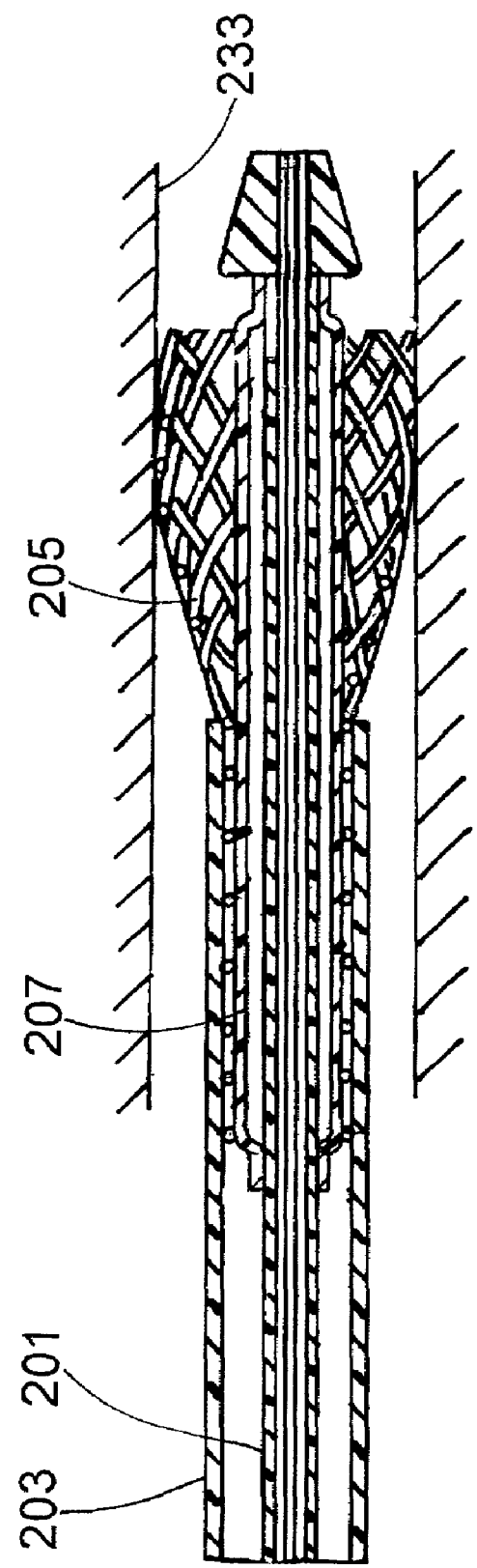
FIG. 4 is a detailed cross sectional view of the distal portion of the stent delivery apparatus in accordance with the first embodiment of the present invention after the stent has been partially deployed in a body lumen.

In certain embodiments of the invention, the balloon may be formed of a material, such as polyethylene terepthalate (PET) or nylon, or combinations thereof, that will expand to a certain nominal size and thereafter have minimal or no further expansion with increasing pressure up to burst pressure. In such embodiments, the balloon nominal radius should be no less than the inner radius of the outer tube minus the wall thickness of the stent. Otherwise the inflated balloon would not contact the stent. While the balloon nominal radius may be larger than the inner radius of the outer tube, preferably, it is somewhere between the inner radius of the outer tube, on the one hand, and the inner radius of the outer tube, minus the wall thickness of the stent, on the other hand. In such embodiments, once any portion of the self expanding stent 205 is released from the outer tube 203, it will expand beyond the diameter of the balloon and engage the wall of the lumen 233, while the balloon diameter does not substantially further expand upon release from the outer tube. FIG. 4 illustrates a partially deployed stent in accordance with such an embodiment. It can be seen that the released, distal portion of the stent 205 has expanded to contact the lumen 233, but the released, distal portion of the balloon 207 remains at substantially the same diameter whether within the outer tube 203 or released from it. Thus, the balloon 207 exerts no radial force on the stent 205 once the stent is released from the outer tube 203. This type of embodiment is preferable because it often is undesirable for the balloon to exert expansive pressure on the body lumen.

However, in some applications, it may be preferable that the balloon be expandable to a greater diameter upon release from the outer tube. In such cases, the balloon may be formed of a more stretchable or elastomeric material, such as polyurethane or silicone. Preferably, however, the balloon pressure still is low enough such that, when the balloon exits the outer tube it expands partially along with the stent, but not sufficiently to contact the body lumen.

The proximal end of the balloon should taper down to a diameter less than the inner diameter of the outer tube as that it can be pulled back in the delivery device after the stent has been released. If the balloon is deflatable, than the taper is immaterial.

The balloon should be formed of a material that is more compliant than the outer tube so that the balloon will take a greater set against the stent than the outer tube and hold it in place longitudinally with respect to the inner tube when the outer tube is moved longitudinally relative to the balloon and stent. If the outer tube was more compliant than the balloon, the stent would take more of a set on the outer tube and thus move along with the outer tube and slide along the surface of the balloon, rather than stay stationary with the balloon and allow the outer tube to slide relative thereto.

Figure 5:
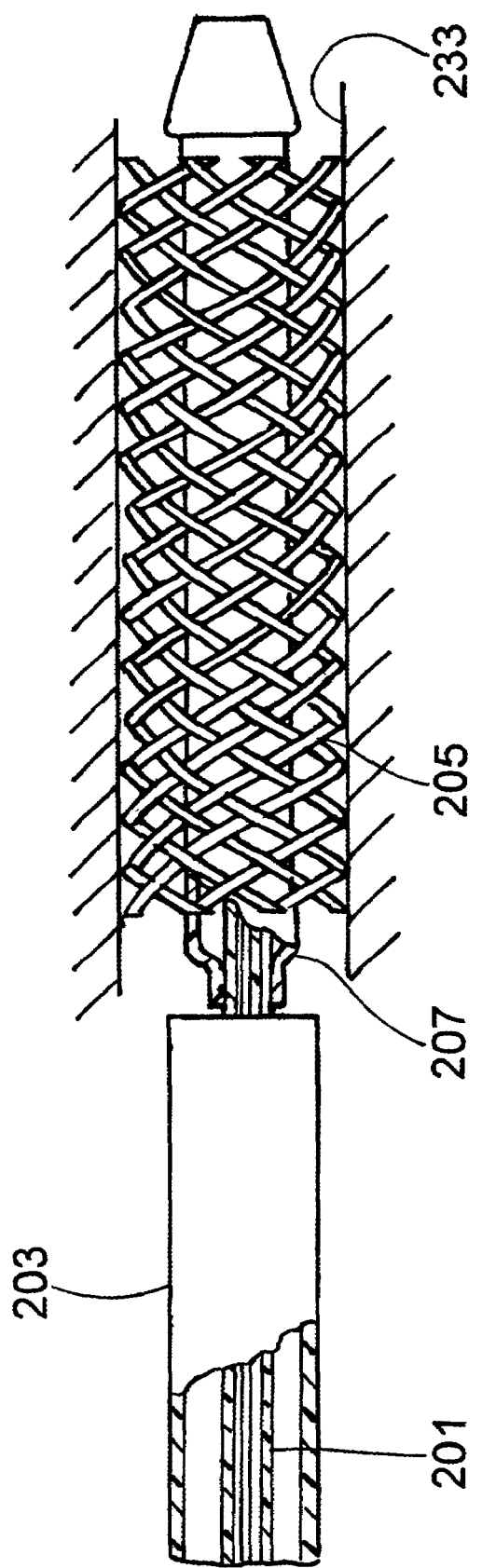
FIG. 5 is a detailed partial cross sectional view of the distal portion of the stent delivery apparatus in accordance with the first embodiment of the present invention after the stent has been fully deployed in a body lumen, but before the balloon has been withdrawn.

The balloon should remain inflated until the stent is fully released from the outer tube and fully engages the wall of the lumen. At any point while the stent and balloon are still partially within the outer tube, the balloon is still holding the stent stationary relative to the inner tube so that the stent can be withdrawn back into the outer tube in case repositioning is necessary after partial release of the stent. FIG. 5 illustrates the stent 205 and stent delivery device 200 in accordance with the first embodiment of the invention after the stent 205 has been fully released from the device 200, but before the balloon 207 has been deflated.

Figure 6:
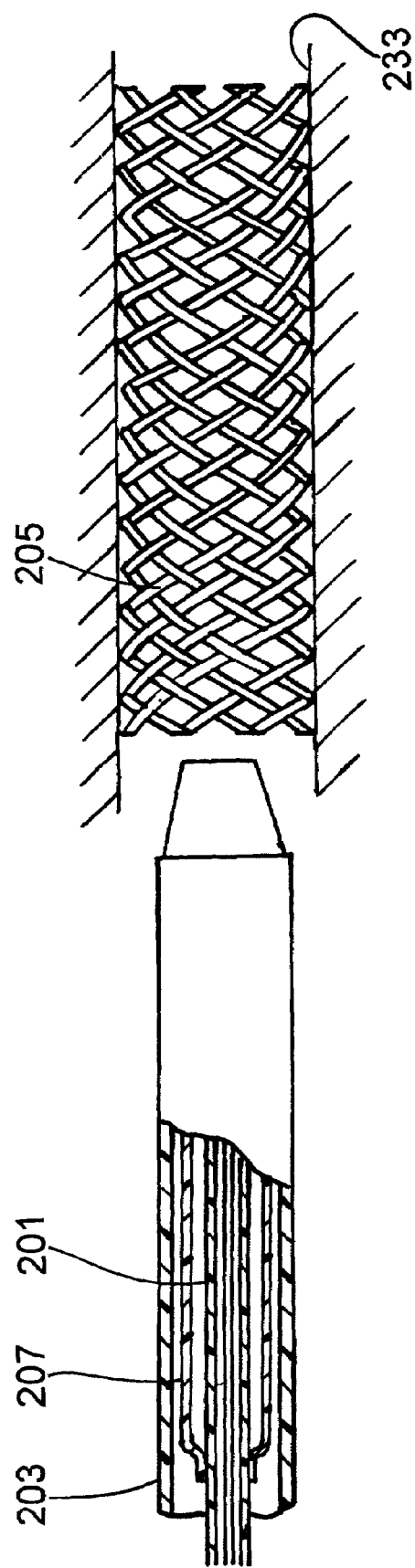
FIG. 6 is a detailed partial cross sectional view of the distal portion of the stent delivery apparatus in accordance with the first embodiment of the present invention after the stent has been fully deployed in a body lumen and the balloon has been withdrawn.

Once the stent is fully released, the balloon can be deflated (for embodiments for which the balloon is not fully sealed in the inflated state) and the inner tube and balloon withdrawn proximally back into the tube as illustrated in FIG. 6. The stent delivery device can then be removed from the lumen and the procedure concluded. With respect to embodiments of the invention in which the balloon is fully sealed, the proximal end of the balloon should taper down to a diameter smaller than the inner diameter of the outer tube, as shown, so that the proximal end of the balloon will easily fit back into the outer tube. Even if the remainder of the inflated balloon has a larger diameter than the outer tube, once the smaller end of the balloon is in the outer tube, the diameter of the remainder of the balloon will shrink when it engages the outer tube as it is pulled proximally relative to the outer tube.

Figure 7A:
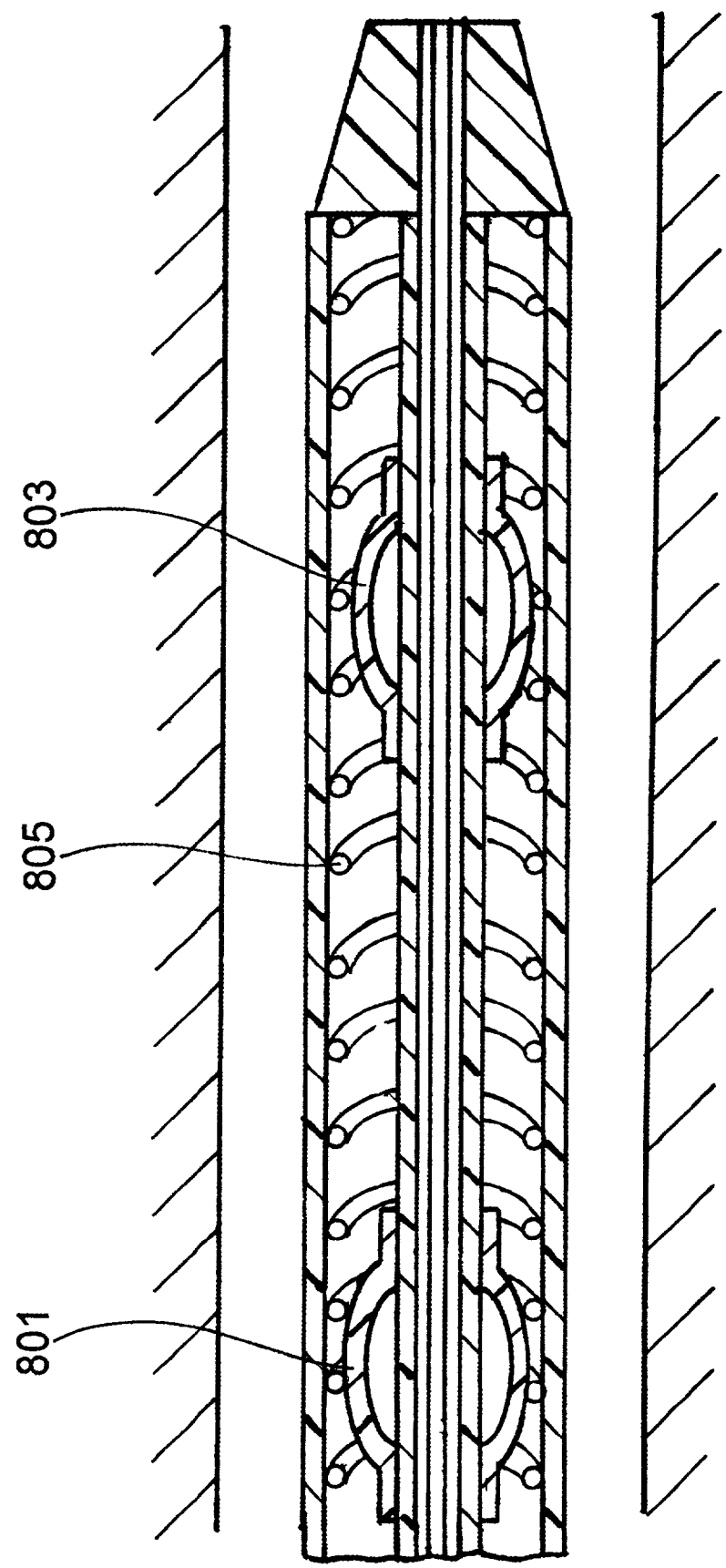
FIGS. 7A and 7B are detailed cross sectional views of the distal portion of the stent delivery apparatus during the initial stage of inserting a self expanding stent into the stent delivery apparatus illustrating various embodiments of the balloon.
Figure 7B:
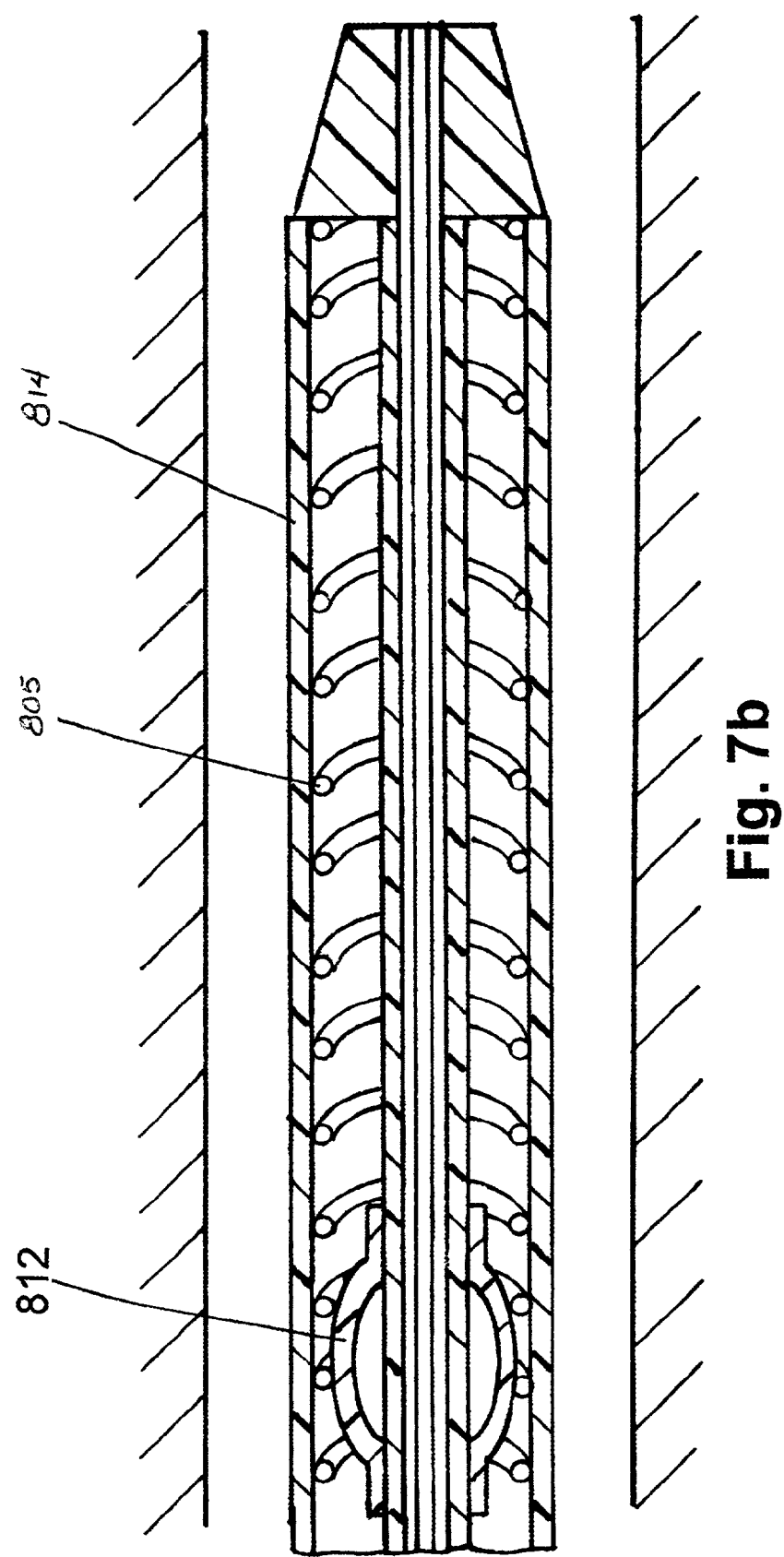

The single balloon of about equal length to the stent illustrated in the preceding Figures is merely exemplary. FIGS. 7A and 7B illustrate various potential embodiments of the invention with different balloon configurations. For instance, FIG. 7A shows an embodiment in which two balloons 801, 803 are used to hold the stent 805 in place. The first balloon 801 is positioned adjacent the distal end of the stent 805 and the second balloon 803 is positioned adjacent the proximal end of the stent 805.

FIG. 7B shows another embodiment in which there is only one small balloon 812 positioned adjacent the proximal end of the loaded stent 805. It should be understood that once the balloon 812 exits the outer tube 814, it no longer serves its primary function of forcing the stent 805 against the outer tube 814. Accordingly, the balloon or at least part of a balloon should be as close to the proximal end of the stent as possible since that is the last part of the stent that can be released from the outer tube. Once the proximal end of the stent is released, the balloon's function is completed since the stent generally cannot be recaptured into the outer tube after that point.

While the invention has hereinabove been described in connection with a standard type of self-expanding stent, it is equally applicable to other forms of stents and, in fact, any tubular self-expanding prosthesis that is delivered in the same general manner. For instance, the invention is equally applicable to stent-grafts and covered stents, both of which are stent-based medical prostheses that are well known to those of skill in the related arts. In fact, it is not even necessary that the prosthesis be self expanding. The invention can be useful in connection with any prosthesis that must be inserted into a small opening.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

We claim:

1. A method for delivering a stent into a body lumen, said method comprising the steps of:
   (1) providing a stent delivery device comprising an outer tube having a proximal end and a distal end and sized to hold said stent therein in a radially constricted condition, an inner tube within said outer tube having a proximal end and a distal end, and a balloon fixedly mounted on said inner tube and positioned within said outer tube;
   (2) positioning said stent in a radially constricted state within said outer tube in a longitudinal position so that at least a portion of said stent is longitudinally contiguous with at least a portion of said balloon;
   (3) inflating said balloon so as to trap said stent between said balloon and said outer tube;
   (4) guiding said delivery device within said body lumen to position said stent within said delivery device to a position within said body lumen; and
   (5) moving said outer tube proximally relative to said inner tube, said balloon and said stent so as to at least partially release said stent from said outer tube.

2. The method of claim 1 further comprising the step of:
   (6) moving said outer tube distally relative to said inner tube, said balloon and said stent so as to at least partially recapture said stent within said outer tube.

3. The method of claim 1 wherein step (3) is performed before step (4) and after step (2).

4. The method of claim 1 wherein step (4) is performed before step (3).

5. The method of claim 1 wherein step (3) is performed as part of the process of manufacturing said stent delivery device.

6. The method of claim 5 wherein step (2) is performed after step (1).

7. The method of claim 6 wherein step (2) is performed just prior to step (4).

8. The method of claim 1 further comprising the steps of:
   (7) deflating said balloon after said stent is fully released from said outer tube;
   (8) moving said inner tube proximally relative to said outer tube so as to recapture said deflated balloon in said outer tube.

9. The method of claim 8 further comprising the step of:
   (9) withdrawing said stent delivery device from said body lumen.

10. The method of claim 1 wherein said stent is a self-expanding braided stent.

11. The method of claim 8 wherein said stent is a self-expanding braided stent.

12. The method of claim 1 wherein step (3) comprises inflating said balloon sufficiently to hold said stent stationary relative to said outer tube when said outer tube is moved longitudinally relative to said inner tube.

13. The method of claim 1 wherein step (3) comprises inflating balloon through said inner tube.

14. The method of claim 1 wherein step (1) comprises providing an inflation tube within said outer tube separate from said inner tube and wherein step (3) comprises introducing a fluid into said balloon via said inflation tube.

15. The method of claim 1 wherein said balloon has a nominal outer diameter beyond which further expansion is minimal with increasing pressure that is smaller than a diameter of said body lumen.

16. The method of claim 1 wherein said outer tube has an inner diameter, said stent has a thickness, and said balloon has a nominal outer diameter beyond which further expansion is minimal with increasing pressure, said nominal outer diameter of said balloon being less than said inner diameter of said outer tube but greater than said inner diameter of said outer tube minus said thickness of said stent.

17. The method of claim 1 wherein said balloon is formed of a material that is more compliant than a material from which said outer tube is formed.

18. A method for delivering a stent into a body lumen, said method comprising the steps of:
   (1) providing a stent delivery device comprising an outer tube having a proximal end and a distal end and sized to hold said stent therein in a radially constricted condition, an inner tube within said outer tube having a proximal end and a distal end, and a balloon fixedly mounted on said inner tube and positioned within said outer tube;
   (2) positioning said stent in a radially constricted state within said outer tube in a longitudinal position so that at least a portion of said stent is longitudinally contiguous with at least a portion of said balloon;
   (3) inflating said balloon so as to trap said stent between said balloon and said outer tube;
   (4) guiding said delivery device within said body lumen to position said stent within said delivery device to a position within said body lumen; and
   (5) moving said outer tube proximally relative to said inner tube, said balloon and said stent so as to at least partially release said stent from said outer tube;
   wherein said balloon is shorter than said stent and wherein step (2) comprises positioning at least a portion of said stent longitudinally aligned with said balloon.

19. A method for delivering a stent into a body lumen, said method comprising the steps of:
   (1) providing a stent delivery device comprising an outer tube having a proximal end and a distal end and sized to hold said stent therein in a radially constricted condition, an inner tube within said outer tube having a proximal end and a distal end, and a balloon fixedly mounted on said inner tube and positioned within said outer tube;

(2) positioning said stent in a radially constricted state within said outer tube in a longitudinal position so that at least a portion of said stent is longitudinally contiguous with at least a portion of said balloon;

(3) inflating said balloon so as to trap said stent between said balloon and said outer tube;

(4) guiding said delivery device within said body lumen to position said stent within said delivery device to a position within said body lumen; and (5) moving said outer tube proximally relative to said inner tube, said balloon and said stent so as to at least partially release said stent from said outer tube;

wherein said balloon is shorter than said stent, said stent having a proximal end and a distal end and wherein step (2) comprises positioning said stent so that said balloon is adjacent said proximal end of said stent.

20. The method of claim 19 wherein said balloon comprises first and second balloons and wherein step (2) comprises positioning said stent so that said first balloon is close to said proximal end of said stent and said second balloon is close to said distal end of said stent.

* * * * *